United States Patent [19]

Iwaguchi et al.

[11] Patent Number: 5,134,156
[45] Date of Patent: Jul. 28, 1992

[54] PHARMACEUTICAL COMPOSITION AND METHOD FOR ANGIOGENESIS INHIBITION

[75] Inventors: Takao Iwaguchi; Mariko Shimamura, both of Tokyo; Shingo Uchida, Yokohama; Takaaki Aoyagi, Fujisawa; Tomio Takeuchi, Tokyo, all of Japan

[73] Assignee: Zaidan Hojin Biseibutsu Kagaku Kai, Tokyo, Japan

[21] Appl. No.: 585,009

[22] Filed: Sep. 19, 1990

[30] Foreign Application Priority Data

Sep. 22, 1989 [JP] Japan .................................. 1-245204

[51] Int. Cl.5 .............................................. A61K 31/40
[52] U.S. Cl. .................................................... 514/423
[58] Field of Search .......................................... 514/423

[56] References Cited

U.S. PATENT DOCUMENTS 4,663,342  5/1987  Umezawa et al. ................... 514/423

FOREIGN PATENT DOCUMENTS 0167936  1/1986  European Pat. Off. ............ 514/423
8801166  2/1988  World Int. Prop. O. ........... 514/159

OTHER PUBLICATIONS

Journal of Cancer Research and Clinical Oncology, vol. 116, suppl., 16th–22nd Aug. 1990, p. 14, abstract No. A1.064.05, Hamburg, Germany; M. Shimamura, et al: "Actinonin a proteinase inhibitor, potently inhibits angiogenesis", p. 14.

Primary Examiner—Jerome D. Goldberg
Attorney, Agent, or Firm—Larson & Taylor

[57] ABSTRACT

Actinonin or a salt thereof is active as an inhibitor of angiogenesis in a mammal and is useful as a therapeutic agent for inhibiting angiogenesis in a mammal having diabetic retinopathy or inflammatory response accompanied by angiogenesis.

2 Claims, No Drawings

PHARMACEUTICAL COMPOSITION AND METHOD FOR ANGIOGENESIS INHIBITION

SUMMARY OF THE INVENTION

This invention relates to a new pharmaceutical composition useful as an angiogenesis inhibitor, which comprises actinonin as active ingredient. This invention also relates to a method for inhibiting angiogenesis in a living mammal, which comprises administering actinonin to a mammal in need of treatment.

BACKGROUND OF THE INVENTION

Actinonin is a known antibacterially active compound which is described in some literatures (see "I.A.M. Symposia on Microbiology, No. 6, Chemistry of Microbial Product" pp. 204–214 (1964) and U.S. Pat. No. 3,240,787 specification) and which is an antibiotic produced by cultivation of a Streptomyces strain (identified as ATCC 14,903 or NCIB 8845). Physicochemical properties of actinonin are alredy known. Actinonin is a compound having the structural formula

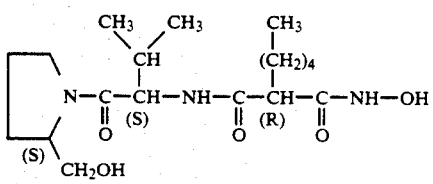

Further, it is known that actinonin exhibits an activity inhibitory to aminopeptidase M, that actinonin is effective as an immunopotentiating agent (Japanese patent application first publication "Kokai" No. 15840/86 and U.S. Pat. No. 4,663,342) and that actinonin is effective as an analgesic agent (Japanese patent application first publication "Kokai" No. 4228/87).

Furthermore, angiogenesis or neovascularization, that is, the development of blood vessels in a mammal takes place through the biological processes comprising migration of vascular endothelial cells, proliferation of these cells and formation of capillary tubes. It is expectable that such diseases having the accompanying angiogenesis, for instance diabetic retinopathy and inflammatory responses can be treated therapeutically by inhibiting the angiogenesis, and it is apparent that a chemical compound which inhibits the angiogenesis would have an adverse effect upon the development of the diabetic retinopathy and inflammatory response (see, for example, U.S. Pat. No. 4,552,888 specification).

We have made researches in an attempt to detect and provide such chemical substances which exhibit an activity inhibitory to the angiogenesis in a mammal, and as a result, we have now found that actinonin shows a remarkably high activity to inhibit the angiogenesis.

This discovery that actinonin shows an angiogenesis-inhibiting activity is a first finding which is now obtained through researches by the present inventors.

DETAILED DESCRIPTION OF THE INVENTION

According to a first aspect of this invention, therefore, there is provided a pharmaceutical composition, useful as an angiogenesis inhibitor, which comprises an effective amount of actinonin or a pharmaceutically acceptable acid addition salt of actinonin as the active ingredient, in association with a pharmaceutically acceptable carrier for the active ingredient.

According to a second aspect of this invention, there is provided a method for inhibiting angiogenesis in a mammal, which comprises administering an effective amount of actinonin or a pharmaceutically acceptable acid addition salt of actinonin to a mammal in need of the treatment.

This invention further includes use of actinonin or a pharmaceutically acceptable acid addition salt thereof in the manufacture of an angiogenesis-inhibiting drug.

The angiogenesis-inhibiting pharmaceutical composition according to this invention comprising actinonin or a salt thereof as the active ingredient may be formulated into various forms suitable for administration, by admixing actinonin or a salt thereof with a pharmaceutically acceptable and conventional solid or liquid carrier or vehicle. The pharmaceutical composition of this invention may further contain one or more of the other, different chemotherapeutic agents.

The pharmaceutically acceptable acid addition salt of actinonin includes a salt with a known pharmaceutically acceptable inorganic acid such as hydrochloric acid, sulfuric acid, phosphoric acid and the like, or a known pharmaceutically acceptable organic acid such as acetic acid, propionic acid, citric acid, oxalic acid and the like.

The pharmaceutically acceptable carrier available in this invention may be a conventional liquid one such as water, ethanol, aqueous ethanol, or a conventional solid one such as starch, casein, talc and the like.

The angiogenesis-inhibiting activity of actinonin is demonstrated with reference to the following test wherein the effect of actinonin to inhibit the angiogenesis in chorio-allantoic membrane (CAM) of the chicken embryo in the incubated chicken egg was estimated.

TEST EXAMPLE (i) Test Method

Fertilized chicken eggs were incubated for 4 days, and one hole was then bored by a gimlet at the top of the air chamber of the incubated eggs and another hole was bored at the lower lateral part of the egg. The white of egg (about 2 ml) was removed by suction at the lower hole of the egg. The air within the air chamber was sucked off through the hole bored at the top of the air chamber of the egg so that the eggshell membrane was released from the chorio-allantoic membrane (CAM) of the chicken embryo. The hole at the lower lateral part of the egg was then sealed. A part of the eggshell was then cut off from the top of the air chamber of the egg and a silicone ring having an inner diameter of 3 mm was placed directly on the chorio-allantoic membrane (having a diameter of 1 to 3 mm) in each egg, followed by pouring a solution (10 $\mu$l) containing a predetermined amount of actinonin and 1% methylcellulose in physiological saline into the silicone ring. The top of the air chamber of the egg was covered by a cap and the eggs were then further incubated for 2 days in an incubator. After this further incubation for 2 days, intralipid was injected into the CAM and the CAM so treated was photographed for estimation of the development of blood vessels.

Degree of inhibition to the angiogenesis was evaluated in term of the following four scales of zero degree to III-degree, according to the method of Crum et al (see Crum R., Szabo S., and Folkman J.; A new class of steroid inhibits angiogenesis in the presence of heparin or a heparin fragment in the "Science" 230, pp.

1375-1378 (1985)). Thus, the degree of inhibition to angiogenesis were estimated as follows:

Zero-degree ... The avasuclar area where the blood vessels were not developed has a size of less than 2 mm in its diameter.

I-degree ... The avascular area has a size of from 2 mm to 4 mm in its diameter.

II-degree ... The avascular area has a size of from 4 mm to 6 mm in its diameter.

III-degree ... The avascular area has a size of greater than 6 mm in its diameter.

(ii) Test Result

The amount of actinonin dosed was in a range of 500 $\mu$g/CAM to 10 $\mu$g/CAM, and it was found that actinonin administered in a dose of 500 $\mu$g to 10 $\mu$g per CAM can inhibit the angiogenesis in the chorio-allantoic membrane in the incubated chicken eggs, and also that actinonin can bring about an inhibition to the development of chorio-allantoic membrane (that is to say, the treatment with actinonin gave chorio-allantoic membranes of smaller dimensions as compared to those of the untreated membranes) simultaneously to the inhibition to the angiogenesis in CAM. However, it was not found that the growth of the chicken embryo as a whole can be inhibited as far as the chicken embryo are visually observed.

In Table 1 below, there are shown the estimated degrees of the angiogenesis-inhibiting activity of actinonin at a dose of 10 to 100 $\mu$g per CAM. The numerial figures given under the scaled degrees of 0, I, II and III for the "Degree of Inhibition" in Table 1 indicate the number of CAM which exhibited respectively the inhibition degrees of 0 to III. It can be observed that actinonin at doses of 10 to 100 $\mu$g per CAM shows an angiogenesis-inhibiting activity and that actinonin even at a dose of 10 $\mu$g/CAM shows a high activity inhibitory to the angiogenesis in CAM.

TABLE 1

| Dose of actinonin | Degree of Inhibition | | | | Total Number of tested CAM |
|---|---|---|---|---|---|
| | 0 | I | II | III | |
| 100 $\mu$g/CAM | 2 | 1 | 1 | 1 | n = 5 |
| 50 $\mu$g/CAM | 1 | 1 | 2 | 1 | n = 5 |
| 10 $\mu$g/CAM | 1 | 2 | 1 | 1 | n = 5 |
| None | 6 | 0 | 0 | 0 | n = 6 |

The above test results reveal that actinonin is a substance which can inhibit the angiogenesis in chorio-allantonic membrane of the chicken embryo without inhibiting the formation of chorio-allantoic membrane. Besides, acute toxicity tests in mice by intravenous injection have shown that no deaths are caused by intravenous administration of actinonin at a dosage of 400 mg/kg, indicating that actinonin is a less toxic substance.

Thus, actinonin exhibits an activity to inhibit the angiogenesis in a mammal and hence, actinonin or a pharmaceutical composition comprising actinonin is useful for therapeutic treatment of diabetic retinopathy and inflammatory diseases, or as an adjuvant or assistant agent for known various agents for use in these therapeutic treatments.

The pharmaceutical composition comprising actinonin as the active ingredient may be prepared by mixing actinonin or a pharmaceutically acceptable salt of actinonin with a conventional, pharmaceutically acceptable carrier.

The administration of actinonin or a pharmaceutical composition containing actinonin may be made by using orally administrable preparations, injectable preparations or rectally administrable preparations containing actinonin or a salt thereof as active ingredient. Lyophilized injections may be prepared by mixing actinonin or a salt thereof with pH-adjustor, buffering agent, stabilizer and excipient and then freeze-drying the resultant mixture by a conventional lyophilization method. Injections for subcutaneous, intramuscular or intravenous administration can be prepared by mixing actinonin or a salt thereof with pH-adjustor, buffering agent, stabilizer, isotonizer and local anesthetic, and then formulating the mixture by known procedures.

For the preparation of orally administrable solid formulations, the active ingredient compound is admixed with excipient, if desired, together with binder, disintegrator, lubricant, colorant, taste-corrective and odor-corrective, whereafter the mixture is formed into tablets, coated tablets, granules, powders and capsules by conventional methods.

For the preparation of orally administrable liquid formulations, the active ingredient compound may be admixed with taste-corrective, buffer, stabilizer and odor-corrective and then the mixture is made into syrups or dry syrup by conventional methods.

To prepare rectal suppositories, the active ingredient compound may be admixed with excipient, if desired, together with surfactant, and the mixture is prepared into suppositories by conventional techniques. The dose of actinonin to be administered to patients may be varied depending on symptoms of the disease, but the usual dosage of actinonin is 1 mg to 200 mg for adult once daily. When concomitant therapy with other chemotherapeutic drugs is to be attempted, actinonin in said dose range may be administered in association with these other drugs in their usual doses.

Some examples of the angiogenesis-inhibiting formulations containing actinonin according to this invention are illustrated with reference to the following Examples 1 and 2, to which this invention is not limited in any way.

FORMULATION EXAMPLE 1

Tablets suitable for oral administration were prepared by mixing the undermentioned ingredients together and compressing the resultant mixture into tablets by a conventional method.

| Ingredients | Proportions |
|---|---|
| Actinonin | 100 mg |
| Lactose | 68.8 mg |
| Corn starch | 20 mg |
| Polyvinyl pyrrolidone | 8.0 mg |
| Magnesium stearate | 1.15 mg |
| Talc | 2.0 mg |
| Coloring agent | 0.05–200 mg |

FORMULATION EXAMPLE 2

Intravenously administrable injection was prepared by mixing the undermentioned ingredients together to produce a uniform solution.

| Ingredients | Proportions |
|---|---|
| Actinonin | 30 mg |
| Sodium hydrogen phosphate | 7.05 mg |

| Ingredients | Proportions |
| --- | --- |
| (anhydrous) | |
| Sodium dihydrogen phosphate (anhydrous) | 6.0 mg |
| Sodium chloride | 5.1 mg |
| Sterilized purified water | Balance to a total volume of 1.5 liters |

We claim:

1. A method of inhibiting angiogenesis in a mammal which comprises administering to a mammal having diabetic retinopathy accompanied by angiogenesis, actinonin or a pharmaceutically acceptable addition salt thereof in an amount sufficient to inhibit the angiogenesis occurring in the mammal.

2. A method of inhibiting angiogenesis in a mammal which comprises administering to a mammal having inflammatory response accompanied by angiogenesis, actinonin or a pharmaceutically acceptable addition salt thereof in an amount sufficient to inhibit the angiogenesis occurring in the mammal.

* * * * *

UNITED STATES PATENT AND TRADEMARK OFFICE
CERTIFICATE OF CORRECTION

PATENT NO. : 5,134,156
DATED : July 28, 1992
INVENTOR(S) : IWAGUCHI ET AL

It is certified that error appears in the above—identified patent and that said Letters Patent is hereby corrected as shown below:

The title page should be changed to show the correct name of the assignee as follows:

[73] Assignee: Zaidan Hojin Biseibutsu Kagaku Kenkyu Kai, Tokyo, Japan

Signed and Sealed this

Twenty-first Day of September, 1993

Attest:

BRUCE LEHMAN

*Attesting Officer*  *Commissioner of Patents and Trademarks*